United States Patent [19]
Zanini-Fisher et al.

[11] Patent Number: 6,133,042
[45] Date of Patent: Oct. 17, 2000

[54] MODULATED OXYGEN-FLUX METHOD AND APPARATUS TO IMPROVE THE PERFORMANCE OF A CALORIMETRIC GAS SENSOR

[75] Inventors: Margherita Zanini-Fisher, Bloomfield Township; Eleftherios M. Logothetis, Birmington; Jacobus H. Visser, Farmington Hills, all of Mich.

[73] Assignee: Ford Global Technologies, Inc., Dearborn, Mich.

[21] Appl. No.: 09/021,154

[22] Filed: Feb. 10, 1998

[51] Int. Cl.[7] .......................... G01N 25/22; G01N 25/30; G01N 33/00
[52] U.S. Cl. .......................... 436/147; 436/133; 436/134; 436/137; 436/139; 436/143; 436/151; 436/152; 436/159; 436/160; 422/94; 422/98
[58] Field of Search ..................................... 436/133, 134, 436/137, 139, 143, 151, 152, 159, 160, 181, 183, 147; 422/83, 90, 94–98

[56] References Cited

U.S. PATENT DOCUMENTS

| 5,250,169 | 10/1993 | Logothetis et al. . |
| 5,451,371 | 9/1995 | Zanini-Fisher et al. . |
| 5,608,154 | 3/1997 | Kato et al. . |
| 5,780,710 | 7/1998 | Murase et al. ........................ 73/1.06 |
| 5,863,803 | 1/1999 | Zanini-Fisher et al. ............... 436/147 |

FOREIGN PATENT DOCUMENTS

| 678740 | 10/1995 | European Pat. Off. . |
| 0849593A3 | 6/1998 | European Pat. Off. . |

OTHER PUBLICATIONS

G.S.U. Coles et al. *J. Phys. D: Appl. Phys.* 1991, 24, 633–641.

Logothetis et al. *Sens. Actuators, B* 1992, B9, 183–189.

J. H. Visser et al. *Sens. Actuators, B* 1992, B9, 233–239.

*Primary Examiner*—Arlen Soderquist
*Attorney, Agent, or Firm*—Damian Porcari; Roger L. May

[57] ABSTRACT

A method and apparatus is provided for modulating the flux of oxygen impinging on a calorimetric gas sensor. The method and apparatus are based on modulating the oxygen concentration of a gas mixture presented to the microcalorimeter between a predetermined high level and at a substantially zero value to create a modulated output to reduce the noise of the sensor and to eliminate its zero-offset.

12 Claims, 2 Drawing Sheets

MODULATED OXYGEN-FLUX METHOD AND APPARATUS TO IMPROVE THE PERFORMANCE OF A CALORIMETRIC GAS SENSOR

FIELD OF THE INVENTION

This invention teaches a method and apparatus for modulating the flux of oxygen impinging on a calorimetric gas sensor to improve the accuracy and the detection limit of the device.

BACKGROUND

Calorimetric gas sensors are potentially useful for measuring on-board the concentration of combustibles in automotive exhaust systems and for correlating increased levels of combustibles with the deterioration of the hydrocarbon (HC) conversion efficiency of an automotive three-way catalyst (TWC).

Si-based calorimetric devices, such as the one described in U.S. Pat. No. 5,451,371, have been shown to have the ability to detect a minimum concentration, called the detection limit, of the order of 10 ppm of $C_1$ when the flow and the temperature of the gas stream are well controlled. This detection limit is sufficiently low to allow the measurement of low hydrocarbon concentration levels in the exhaust gas of newer automotive vehicles. However, in many practical applications, including exhaust gas sensing, the device is exposed to large temperature fluctuations, especially in a high velocity, turbulent flow environment. Such temperature fluctuations produce an increase in the device noise because they cannot be completely compensated for by the differential nature of the device, and, as a result, the device detection limit deteriorates. In addition, the zero-offset of differential calorimeters that are based on the difference between two resistive temperature detectors (RTDs), one being a reference element and the other a sensing element, needs to be accurately trimmed to achieve 10 ppm of $C_1$ calibration accuracy. Furthermore, any drift in the zero-offset during the life of the device reduces the long term accuracy of the sensor. There is thus a need to improve the accuracy and the detection limit of calorimetric gas sensors for measuring exhaust gas constituents.

SUMMARY OF THE INVENTION

Accordingly, the present invention is a method and apparatus for modulating the oxygen concentration of a gas mixture presented to a calorimetric gas sensor to increase the sensor's accuracy and detection limit. The method includes the step of placing the sensing element and the reference element of the calorimetric gas sensor in a first region, preferably a first encasement, to allow the gas mixture to impinge on the sensing and reference elements. The method also includes the step of placing a second encasement, defining a second cavity containing an oxygen reference atmosphere in mating engagement with the calorimetric gas sensor, wherein the area of engagement comprises an oxygen conducting membrane. A pair of electrodes is placed on the two sides of the oxygen conducting membrane to form an electrochemical cell. The method further includes the step of applying a modulated current to the pair of electrodes at a level sufficient to modulate the $O_2$ concentration in the gas mixture in the first cavity at a predetermined high level and at a substantially zero value to produce a modulated output signal from the calorimetric gas sensor. Lastly, the sensor output is measured at the frequency of modulation.

The invention further teaches a method of measuring the concentration of combustibles in a gas stream with a calorimetric gas sensor, wherein the oxygen concentration is modulated in the gas stream by alternately adding oxygen to the gas stream to achieve a predetermined high oxygen concentration and removing oxygen from the gas stream to attain a substantially zero value to produce a modulated output signal from the calorimetric gas sensor. The method further includes the step of measuring the modulated output signal at the frequency of modulation $\omega$.

One feature of the present invention is that the method and apparatus modulate the oxygen concentration of the gas mixture to derive a modulated output from a calorimetric gas sensor. Another feature of the present invention is that a method and apparatus are provided for modulating the oxygen concentration reacting on a calorimetric gas sensor so that the sensor output is measured at the frequency of modulation using phase-sensitive detection techniques to improve the accuracy and detection limit of the sensor. Yet another feature of the present invention is that the method and apparatus improve the detection limit of the calorimetric gas sensor so that it can be used in an environment with large thermal fluctuations. Still another feature of the present invention is that the method and apparatus eliminate the inaccuracy of the calorimetric gas sensor associated with zero-offset drifts.

Other features and advantages of the present invention will be readily appreciated as the same becomes better understood after reading the subsequent description when considered in connection with the accompanying drawings.

BRIEF DESCRIPTION OF THE DRAWINGS

FIG. 3d is a schematic illustration of the modulated output of the calorimetric device for two different concentrations of combustibles when the zero-offset of the device is zero.

DESCRIPTION OF THE PREFERRED EMBODIMENT(S)

The method of the present invention is intended to increase the accuracy and detection limits of calorimetric gas sensors. A simple calorimetric gas sensor is described in U.S. Pat. No. 5,451,371, assigned to Ford Motor Company and incorporated for reference herein. The calorimetric gas sensor described in the '371 patent includes a bulk silicon frame and a polysilicon layer attached to one side of the frame. Within the boundaries of the polysilicon layer are two polysilicon plates which are located in openings in the polysilicon layer. Each of the two polysilicon plates contains a platinum resistor thermometer. One of the polysilicon plates, the sensing element, has on the top surface a catalytic layer deposited thereon while the other, the reference element (having no catalyst deposited thereon) is used for temperature compensation.

When combustibles are present in the ambient gas mixture the exothermic reaction of these molecules with oxygen on the catalytic layer raises the temperature of the sensing element above that of the reference. A measurement of the temperature difference between the two elements provides a measure of the concentration of combustibles in the gas mixture. It is observed that the device response has a linear dependence on the combustibles concentration, in the presence of oxygen in excess of the stoichiometric value, which means that the flux of molecules oxidized on the surface is proportional to the concentration of combustibles in the gas mixture.

Figure 1:
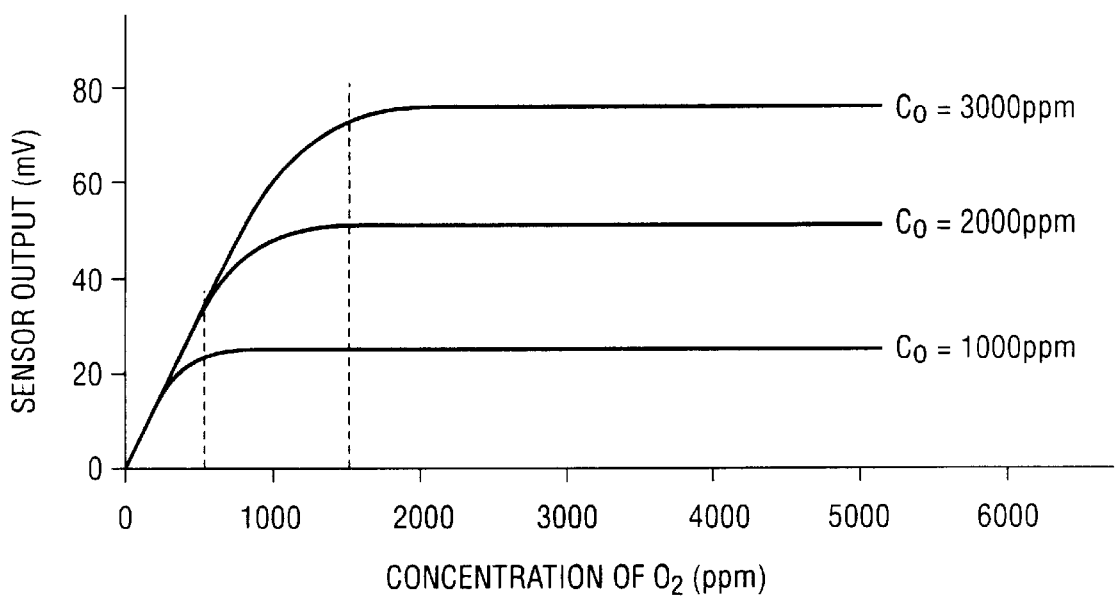
FIG. 1 illustrates the schematic response of the calorimetric sensor for given combustibles concentrations as a function of the oxygen concentration.

FIG. 1 shows the output of a calorimetric sensor as a function of the $O_2$ concentration for three concentrations of CO (1000 ppm, 2000 ppm, and 3000 ppm). Similar results are generally obtained for other combustible gases. For excess $O_2$, the sensor output is approximately constant, but decreases as the $O_2$ concentration is decreased below the stoichiometric value for each of the three gas mixtures (respectively, 500 ppm, 1000 ppm, and 1500 ppm $O_2$, as required by the reaction $CO+\frac{1}{2}O_2 \rightarrow CO_2$). It is clear, that a higher concentration of CO will require a higher concentration of $O_2$ in order to have a gas mixture with excess $O_2$.

As shown in FIG. 1, in order to usefully employ this calorimetric device for the detection of a combustible, e.g. CO, one has to either know the $O_2$ concentration in the gas stream or to always have sufficient $O_2$ SO that the gas stream contains excess $O_2$ even for the highest CO concentrations expected to exist in the gas stream.

The method of this invention achieves an increase in the accuracy and detection limit of the sensor. The method is based on modulating the oxygen concentration presented to the microcalorimeter between two values, one corresponding to an unambiguously excess-oxygen mixture and the other corresponding to a gas mixture with substantially zero $O_2$ concentration. Since the incoming gas mixture generally contains $O_2$, it is necessary in the method of this invention to alternately add and remove $O_2$ from the gas mixture.

The modulation of the $O_2$ concentration between the two values can be most conveniently carried out by using a $ZrO_2$ electrochemical cell. It is well known in the art, that when an electric current is passed through a $ZrO_2$ cell, $O_2$ is transferred ("pumped") from the gas adjacent to the negative electrode to the gas adjacent to the positive electrode. Consequently, when repeatedly at a frequency $\omega$, a current in the proper direction is passed through the $ZrO_2$ cell to add excess $O_2$ in the gas mixture adjacent to the microcalorimetric device, and then a current in the opposite direction is passed through the $ZrO_2$ cell to remove all the oxygen from the gas mixture adjacent to the microcalorimetric device, a modulated output from the device is generated since, for a given CO concentration, the output of the calorimeter is maximum when the $O_2$ concentration is in excess and substantially zero when the $O_2$ concentration is substantially zero. By measuring the device output at the frequency of modulation, for instance using phase sensitive techniques, the zero-offset is eliminated and device noise is reduced. The oxygen-flux modulation is achieved with the apparatus described below. The same apparatus that provides the oxygen-flux modulation makes it possible to use the microcalorimeter to measure combustible species irrespective of whether the incoming gas mixture has $O_2$ in excess of stoichiometry.

The use of a $ZrO_2$ $O_2$-pumping cell to add needed $O_2$ to a gas mixture containing a combustible without $O_2$ (or with only a small amount of $O_2$) in order to be able to measure the concentration of this combustible with a gas sensor (e.g. a $SnO_2$ resistive-type gas sensor) is described in U.S. Pat. No. 4,250,169 assigned to Ford Motor Company.

Figure 2:
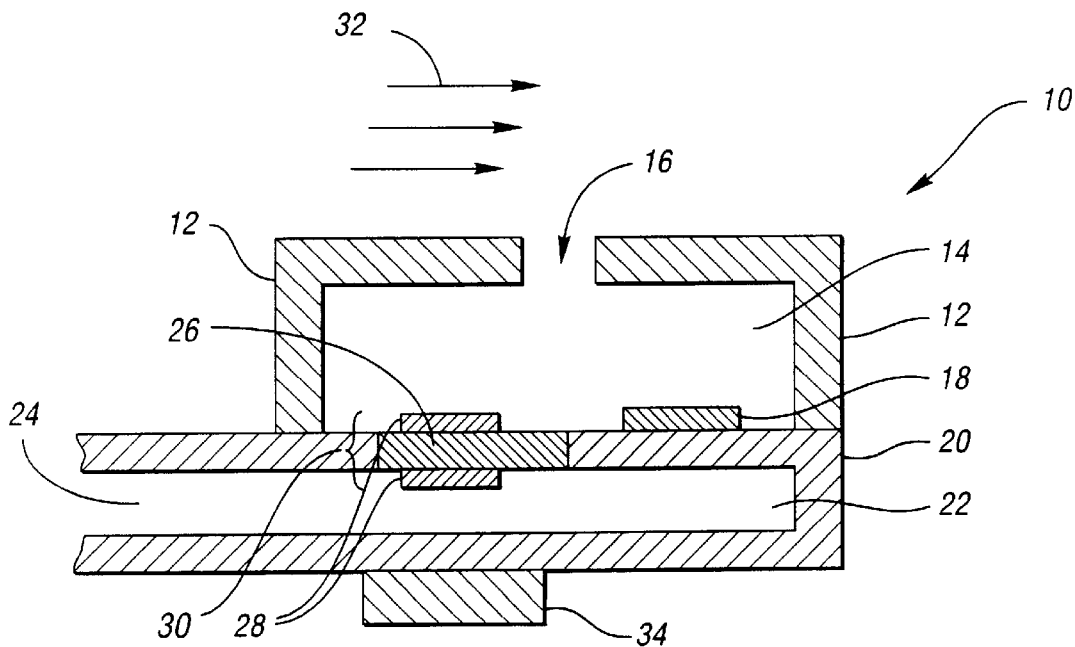
FIG. 2 is a perspective view of a preferred apparatus embodiment of the present invention, illustrated in operational relationship with a microcalorimetric gas sensor.
Figure 3A:
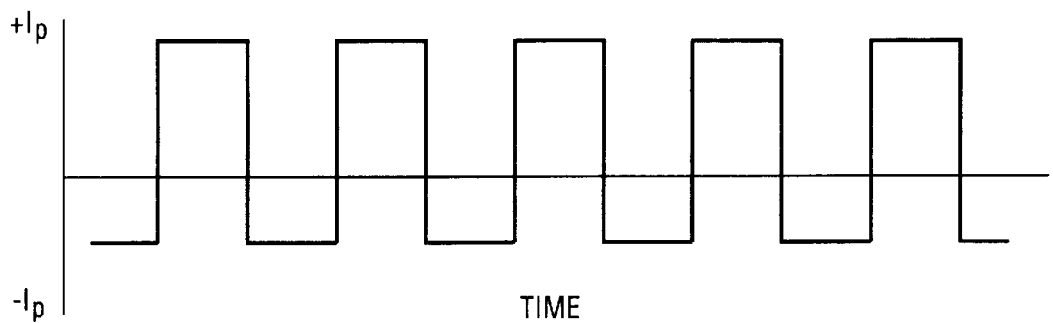
FIG. 3a is a schematic illustration of the pumping current modulation.
Figure 3B:
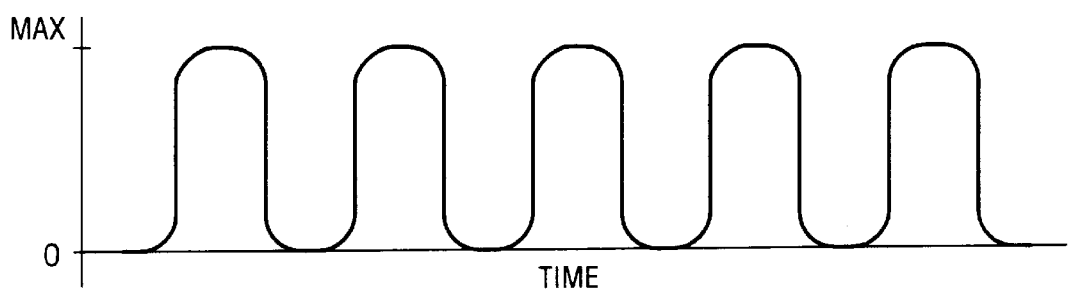
FIG. 3b shows the modulation of the oxygen concentration in the cavity.
Figure 3C:
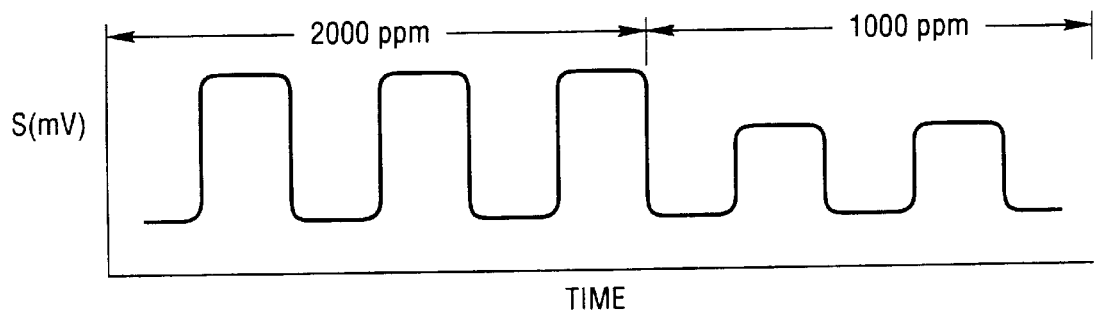
FIG. 3c is a schematic illustration of the modulated output of the calorimetric device for two different concentrations of combustibles, showing that the amplitude of the modulation is a unique function of the combustible concentration.
Figure 3B:
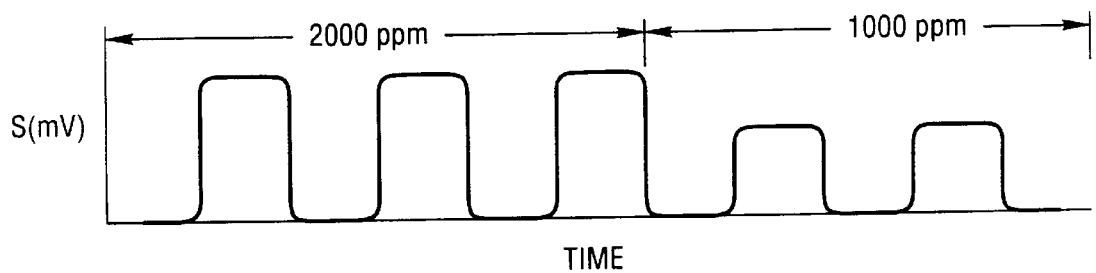

FIG. 2 shows a preferred embodiment according to the present invention wherein apparatus 10 includes a first region, preferably a first encasement 12, defining a first cavity 14 and having at least one aperture 16, enclosing a sensing element and a reference element of a calorimetric gas sensor 18. The first encasement 12 can be rectangular in shape and can be fabricated from ceramic materials. The first encasement 12 has at least one aperture 16 extending through the ceramic material to allow combustibles to enter and impinge on the sensing element and reference element of the calorimetric gas sensor 18. It should be appreciated that the aperture 16 may have any suitable shape. The size of the aperture 16 in the first encasement 12 is optimized to allow a sufficient flux of combustibles in the first cavity 14 to achieve a desired sensor sensitivity, while, at the same time, minimizing the $O_2$ flux escaping from the first encasement 12 to the gas stream when the composition of such gas stream is rich. In the preferred embodiment, the aperture is a circular hole with a diameter in the range of 0.1 millimeters–1 millimeter. It should be understood at this time that any shape or dimension presented herein is based on the presented example and should be varied according to the size of the device and the characteristics of the catalyst. The aperture 16 can also be a slit or any other convenient means for providing communication between first cavity 14 and the incoming gas mixture 32.

With continuing reference to FIG. 2, the apparatus of the present invention, further includes a second or reference encasement 20, defining a second cavity 22 containing an oxygen reference atmosphere. An oxygen reference atmosphere is defined herein as an atmosphere having a predefined oxygen concentration to serve as a source of $O_2$. For example, air is a convenient reference atmosphere.

The area of engagement between the first encasement 14 and the second or reference encasement 20 comprises an oxygen conducting membrane 26. The wall separating the first and second cavities 14,22 is preferably composed of alumina with an embedded $ZrO_2$ oxygen conducting membrane 26 at the area of engagement. The second cavity 22 is connected to ambient air 24. Alternatively, the entire wall can be made of $ZrO_2$.

In the preferred embodiment, and as depicted in FIG. 2, a pair of electrodes 28 are placed on the conducting membrane 26, the pair having an electrode on opposite sides of the membrane 26 and in each of the first and second cavities 14,22. The pair of electrodes are preferably composed of a material with low catalytic activity so that negligible oxidation of the combustible species occurs thereon. With these constraints, the electrode material is preferably composed of gold, silver or gold-platinum alloys. Conducting membrane 26 and pair of electrodes 28 form a solid state electrochemical cell 30. Pursuant to the method of this invention, by applying an appropriate bias to the electrochemical cell 30, a flux of oxygen can be pumped either in or out of the first cavity 14 to modulate the oxygen concentration therein. Additionally, a heater 34 may be included with the apparatus 10 to provide heat and maintain the apparatus 10 at a desired temperature.

In operation, and under the method of this invention, the concentration of oxygen in cavity 14 is modulated between substantially zero and a concentration level higher than the stoichiometric value of the gas mixture 32 in cavity 14. This produces a modulated sensor output since the microcalorimeter output is reduced to zero when the amount of oxygen in the gas mixture impinging on the sensor is zero. In addition, this AC signal is largely independent of the zero-offset drift, resulting in an increase of accuracy in the calorimetric gas sensor 18.

Additionally, according to the present invention, a method is provided for modulating the flux of oxygen impinging on the calorimetric gas sensor 18. The method includes the step of enclosing the sensing element and the reference element of a calorimetric gas sensor in a first encasement 12, defining a first cavity 14 and having at least one aperture 16 to allow combustibles to enter and impinge on the sensing element and the reference element. The method also includes the step of placing a second or reference encasement 20, defining a second cavity 22 and having at least one aperture 24, in mating engagement with the calorimetric gas sensor 18. The area of engagement comprises an oxygen conducting membrane 26. A pair of electrodes 28 is then placed on the conducting membrane 26, each pair having an electrode on opposite sides of the membrane 26 and in each of the first and second cavities 14,22.

The method further includes the step of applying a modulated current or voltage to the first pair of electrodes to modulate the $O_2$ concentration of the gas mixture 32 in the first cavity 14 at a desired high level and at a substantially zero value to produce a modulated output signal from the calorimetric gas sensor. Lastly, the sensor output is measured using, for instance, phase sensitive detection techniques.

EXAMPLES

We use CO as the combustible species for the example, although the same model is valid for hydrocarbons. In this example, based on the characteristics of the catalyst and the size of the sensor, the first cavity was made in the shape of a box with a base of 6×10 $mm^2$ and a height of 1 mm. This cavity can accommodate a microcalorimetric sensor in the shape of a thin plate with dimensions of 6×6 $mm^2$. However, a smaller cavity may be utilized if the sensor dimensions are proportionally reduced, for example, 3×3 $mm^2$, a size suitable for production.

The $O_2$-pumping electric current through the $ZrO_2$ cell 30 is modulated between a predetermined positive value (corresponding to pumping a predetermined flux of oxygen from the reference atmosphere into cavity 14) and a predetermined negative value (corresponding to pumping all the oxygen from cavity 14 into the reference atmosphere). To achieve modulation frequencies of the order of 10 Hz so that the device response remains of the order of 1 sec, the volume in the cavity needs to be kept in the range one to one tenth of the volume equivalent to the number of combustible molecules reacted in one second. This condition is easily met because the microcalorimeter structure is small.

The type of modulation can be chosen to be one of a number of possible waveforms, for example, a square-wave or a sinusoidal waveform. The positive value of the amplitude $I_p$ of the modulated current can be determined once the range of possible concentrations in gas mixture 32 and the desirable device sensitivity are known. Some constraints have already been mentioned: for example, this positive current $I_p$ cannot exceed the maximum value that the electrochemical cell 30 is able to supply; also, the $O_2$ flux transferred by the current $I_p$ cannot exceed the maximum $O_2$ flux that the reference atmosphere can supply. The negative value of the amplitude $I_n$ of the modulated current can be determined once the maximum value of the $O_2$ concentration in gas mixture 32 is known.

As an illustration of this invention, FIG. 3 shows schematically the response of a calorimetric device to two different CO concentrations (1000 ppm and 2000 ppm) in gas mixture 32 for a square-wave modulation of the electric current of electrochemical cell 30 at a frequency of 10 Hz. In this example, it is assumed that only the CO concentration is changed in gas mixture 32. The response characteristics of this calorimetric device to CO and $O_2$ are assumed to be as those shown in FIG. 1. FIG. 3a shows the electric current waveform whereas FIG. 3b shows the resulting $O_2$ concentration in cavity 14. FIG. 3c shows the output of the calorimetric device as a function of time for two CO concentrations (1000 ppm and 2000 ppm) when the zero-offset of the device is positive. FIG. 3d schematically illustrates the modulated output of the calorimetric device for the same two concentrations of combustibles when the zero offset of the device is zero. It is clear from these Figures that the AC component of the output of the calorimetric device at the modulation frequency is independent of the value of the zero-offset. In addition, by measuring the output at 10 Hz with a small bandwidth, for example 1 Hz, the device noise generated by the time-dependent difference in the "background" temperatures of the sensing and the compensating elements of the calorimetric device is greatly reduced.

In an alternate embodiment, instead of measuring the AC component of the sensor output at the modulation frequency ω, the sensor output component at some harmonic frequency can be also measured; or, instead, one can make a DC measurement of the sensor output when the modulation current is at its maximum positive value and a similar measurement when the modulation current is at its maximum negative value and then subtract the two measured values. It is also clear that the present invention is applicable not only to calorimetric gas sensors but also to other gas sensors the response of which depends similarly on the $O_2$ concentration. Even if the $O_2$-dependence of those other gas sensors is different, it is most likely possible to develop an $O_2$-concentration modulation method analogous to the one described in this invention and thus achieve the same benefits of improved detection limit and elimination of the effect of the zero-offset drift.

The present invention has been described in an illustrative manner. It is to be understood that the terminology which has been used is intended to be in the nature of description rather than of limitation. Many modifications and variations of the present invention are possible in light of the above teachings. Therefore, within the scope of the appended claims, the present invention may be practiced other than as specifically described.

What is claimed is:

1. A method of measuring the concentration of combustibles in a gas stream with a calorimetric gas sensor, comprising:

modulating the oxygen concentration in the gas stream by alternately adding oxygen to the gas stream to achieve a predetermined oxygen concentration and removing oxygen from the gas stream to attain a substantially zero value to produce a modulated output signal from the calorimetric gas sensor; and measuring the modulated output signal at the frequency of modulation ω.

2. The method of claim 1, wherein the oxygen concentration is modulated in the portion of the gas stream impinging on the calorimetric gas sensor.

3. A method of measuring the concentration of combustibles in a gas stream with a calorimetric gas sensor, the method comprising the steps of:

placing a sensing element and a reference element of the calorimetric gas sensor in a first region defining a first cavity to allow the gas stream to impinge on the sensing element and the reference element;

placing a reference encasement, defining a second cavity which contains an oxygen reference atmosphere, in mating engagement with the calorimetric gas sensor, wherein the area of engagement comprises an oxygen conducting membrane with a pair of electrodes thereon;

applying a modulated AC current at frequency $\omega$ to the pair of electrodes of sufficient magnitude to modulate the $O_2$ concentration of the gas stream in the first cavity at a predetermined level and at a substantially zero value to produce a modulated output signal from the calorimetric gas sensor; and measuring the sensor output at the frequency of modulation $\omega$.

4. A method of measuring the concentration of combustibles in a gas stream with a calorimetric gas sensor to increase its accuracy and detection limit, the method comprising the steps of:

enclosing a sensing element and a reference element of the calorimetric gas sensor in a first encasement, defining a first cavity, having at least one aperture to allow a portion of the gas mixture to impinge on the sensing element and reference element;

placing a second encasement, defining a second cavity which contains an oxygen reference atmosphere in mating engagement with the calorimetric gas sensor, wherein the area of engagement comprises an oxygen conducting membrane with a pair of electrodes thereon, the pair of electrodes having an electrode in each of the first and second cavities;

applying a modulated AC current at frequency $\omega$ to the pair of electrodes of sufficient magnitude to modulate the $O_2$ concentration of the gas mixture in the first cavity at a predetermined level and at a substantially zero value to produce a modulated output signal from the calorimetric gas sensor; and measuring the sensor output at the frequency of modulation $\omega$.

5. The method of claim 4, wherein the second cavity further contains an aperture in communication with air.

6. The method of claim 4, further comprising the step of optimizing the size of the at least one aperture of the first encasement to allow a sufficient flux of combustibles in the first cavity to achieve a desired sensor sensitivity.

7. The method of claim 4, wherein the at least one aperture of the first encasement has a diameter in the range of 0.1 mm to 1 mm.

8. The method of claim 4, wherein the second encasement is composed of alumina.

9. The method of claim 4, wherein the conducting membrane is composed of zirconium oxide.

10. The method of claim 4, wherein the electrode in the first cavity comprises a material with low catalytic activity for the oxidation of combustibles.

11. The method of claim 10, wherein the electrode is selected from the group consisting of gold, silver, and gold-platinum alloys.

12. The method of claim 4, further comprising the step of providing a heater in mating engagement with the second encasement.

* * * * *